United States Patent [19]
Camp

[11] 4,182,325
[45] Jan. 8, 1980

[54] STEAM-AIR INHALATOR

[76] Inventor: Nat Camp, 912 Sunset Ave., Gettysburg, Pa. 17325

[21] Appl. No.: 868,569

[22] Filed: Jan. 10, 1978

[51] Int. Cl.² ............................................. A61M 15/00
[52] U.S. Cl. ................................................. 128/203.27
[58] Field of Search ................... 128/209, 210, 173.1, 128/173.2, 173.3, 186, 192, 193, 194, 195, 196, 197, 205, 367, 368; 261/78 A, DIG. 76

[56] References Cited
U.S. PATENT DOCUMENTS

| | | | |
|---|---|---|---|
| 73,913 | 1/1868 | Miles | 128/186 |
| 3,588,057 | 6/1971 | Breiling | 128/188 X |
| 3,743,780 | 7/1973 | Camp | 128/192 X |
| 3,894,537 | 7/1975 | Camp | 128/193 |

FOREIGN PATENT DOCUMENTS 111495  9/1940  Australia ................................. 128/186

Primary Examiner—Henry J. Recla
Attorney, Agent, or Firm—Fidelman, Wolffe & Waldron

[57] ABSTRACT

A steam and air mixing chamber having a downwardly open housing is mounted on top of a steam generator located in a housing containing a water reservoir. A steam nozzle directs a jet of steam against a baffle mounted in the mixing chamber entraining air and forming a mist. Compressed air is directed into the mixing chamber by a venturi sucking the mist and causing the mixture to flow into a T joint having one arm connected to a breathing element. A port in the T joint receives a carrier for volatile medicament. A vertical arm of the T is connected to a tube which returns condensate to the water in the reservoir.

10 Claims, 7 Drawing Figures

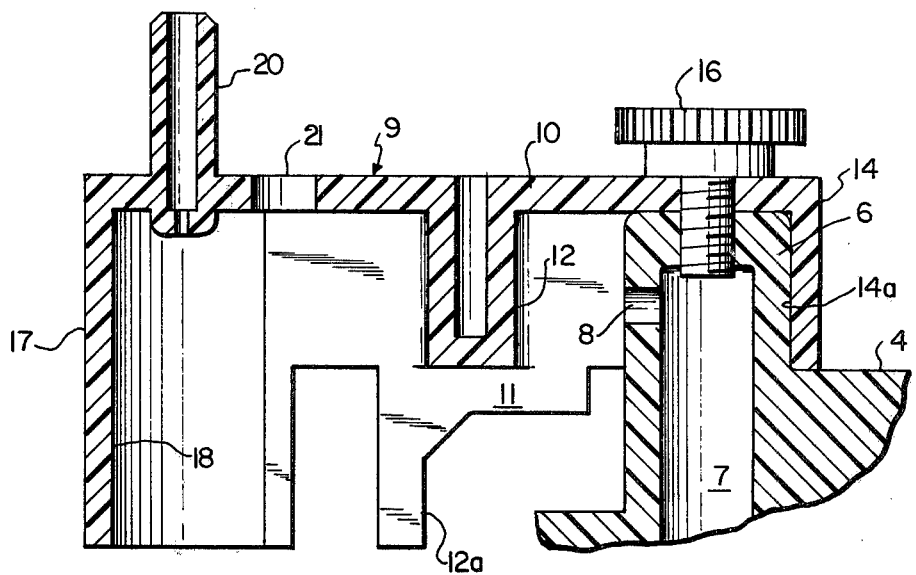
FIG. 3
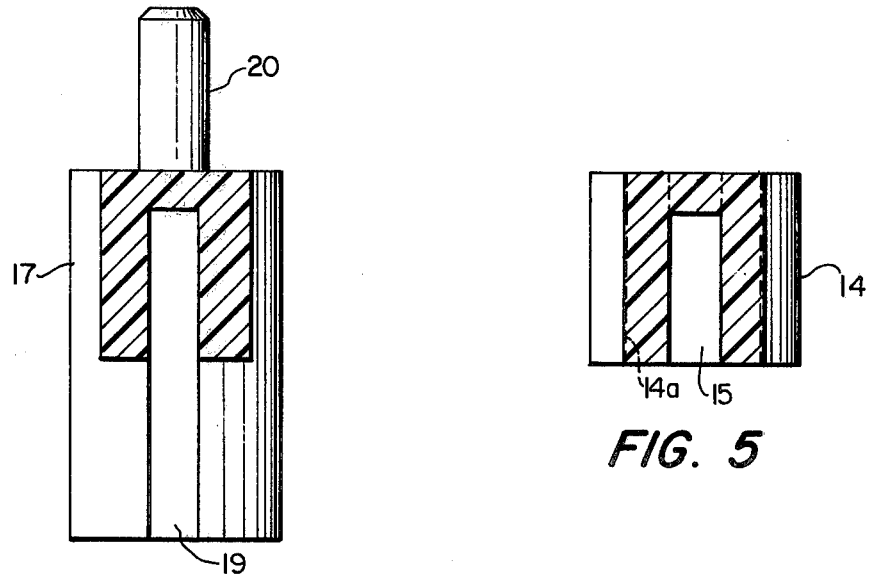
FIG. 4
FIG. 5

STEAM-AIR INHALATOR

FIELD OF THE INVENTION

This invention relates to a steam-air inhalator device for converting water vapor to a fine mist, to be used, for example, to supply moist air or oxygen to a patient for breathing purposes.

BACKGROUND OF THE INVENTION

Nebulizers are known in which preheated water is driven in a thin stream against a target so as to break up into small particles which mix with the surrounding air in order to moisturize same. Other systems use ultrasonic vibrations to fragmentize the water stream. It is generally desired to make the particle size as small as possible, preferably of 5 microns or less, so as to facilitate penetration of the water particles into the respiratory tract of a patient. However, the mist produced in this manner is not very stable since the water particles are not uniformly dispersed in the airflow and tend to coalesce, thereby forming larger droplets which settle out prematurely in the supply conduit as well as in the respiratory tract itself. The equipment is relatively inefficient, complex and correspondingly expensive, especially for home use; moreover, unless the water is pre-boiled, sterile conditions are difficult to maintain.

In U.S. Pat. 3,894,537, which is incorporated herein by reference, I have described an effective steam-air inhalator which gives very satisfactory results. The present invention is an improvement over this patent in that provision is made for incorporating medication in moist air, or oxygen, or oxygen-rich air and also for returning condensate to the steam generator.

It is a general object of this invention to provide an improved inhalator for producing a stable mist of sub-micron particles.

A further object is to provide means to return condensate formed in the breathing element to the steam generator.

Yet a further object is to provide a means for incorporating volatile medicaments within the mist so that a medicated breathing mist is produced.

SUMMARY OF THE INVENTION

I realize these objects, in accordance with my present invention, by providing a mixing chamber whose housing has an internal channel partly obstructed by a generally transverse baffle, the housing having an entrance for ambient air communicating with the channel in the vicinity of the baffle. A channel inlet on one side of the baffle has means for directing a jet of steam against the baffle whereby steam is deflected into the surrounding air to form a mist. The surrounding air is constantly aspirated from the ambient atmosphere through the aforementioned entrance with the aid of suction means communicating with the channel on the opposite side of the baffle. An outlet for discharging the mist-laden aspirated air from the channel is provided.

The housing is open at its underside, forming a channel, and the nozzle directs a jet of steam against a baffle located within the channel. Ambient air is drawn into the channel and a superfine mist is formed. At the end of the channel a venturi fitting is located and compressed air, oxygen, or enriched air is passed through the venturi. The mist plus additional air is thereby forced into a T connection having a lateral arm attached to a breathing mask or a mouth piece. A carrier having volatile medicament thereon may be inserted through a port in the T connection whereby the mist can be medicated, as for example with antibacterial and decongestant agents. One end of the T connection can extend into the water in the reservoir and serve as a condensate return tube.

BRIEF DESCRIPTION OF THE DRAWING

FIG. 3 is a sectional view of the inhalator.

FIGS. 4 and 5 are sections along lines 4—4 and 5—5 in FIG. 2.

Figure 1:
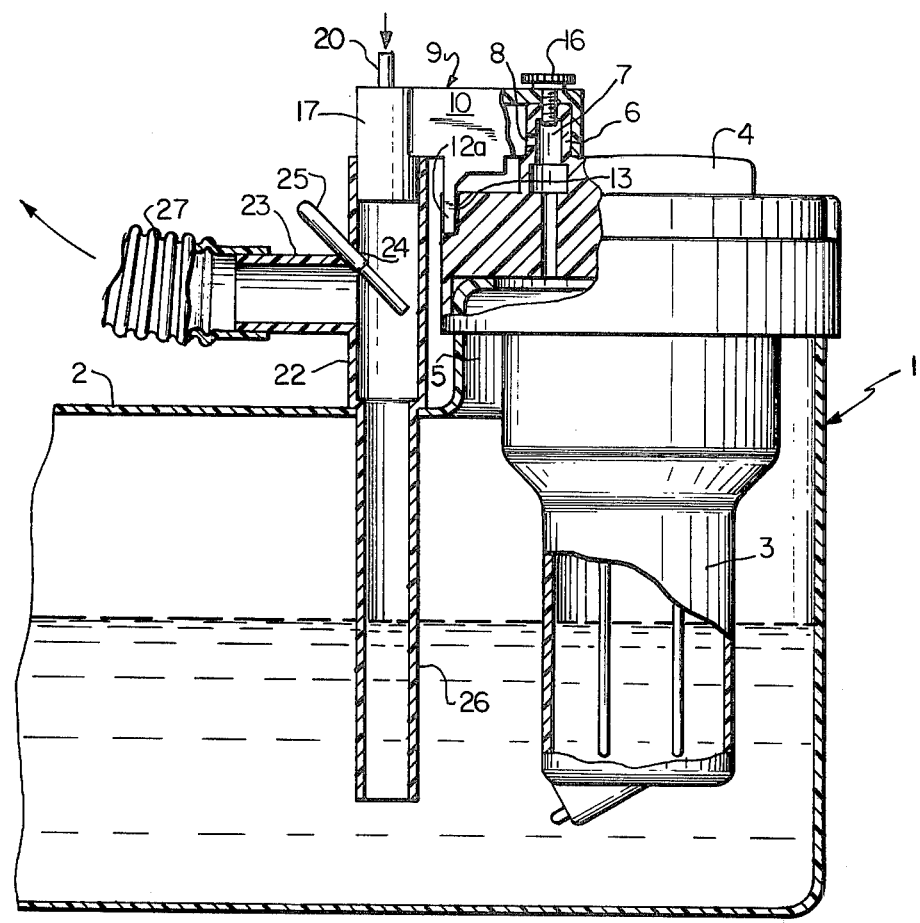
FIG. 1 is an elevational view with parts in section of the inhalator apparatus according to my invention.

The apparatus shown in FIG. 1 comprises a vaporizer 1 having a top surface 2, only a portion of the vaporizer being shown. Advantageously this has the construction of the steam generator disclosed in my prior U.S. Pat. No. 3,743,780. A boiling unit 3 having a top surface 4 and a pair of electrodes encased therein, fits into a raised opening 5 in the top surface of the vaporizer. Steam nozzle 6, which is integrally formed with the top surface 4, has a passageway 7 connected with the boiler for the passage of steam generated therein, and an orifice 8.

Figure 2:
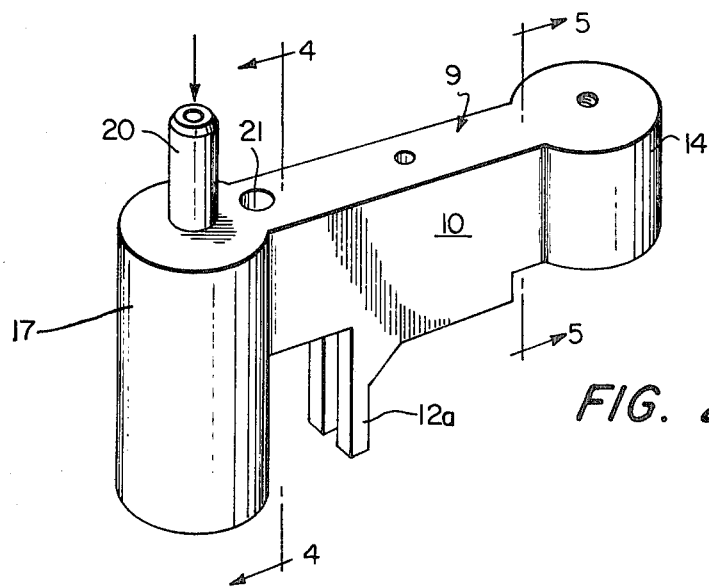
FIG. 2 is a perspective view of the inhalator.

A steam-air mixing chamber 9 has a housing 10 with an internal channel 11 open at the bottom. This channel is partially obstructed by a transverse baffle 12 depending from the closed top of the housing. Depending lugs 12a on the bottom of the housing are adapted to fit into a notch 13 in the top surface of the boiling unit and aids in retaining the mixing chamber in place. One end of the housing 10 is generally cylindrical as shown at 14 having as shown in FIGS. 3 and 5 an internal bore 14a adapted to receive the steam nozzle 6. Bore 14a has a slot 15 in line with orifice 8 in the nozzle. To retain mixing chamber 9 on the vaporizer, screw 16 passes through the mixing chamber at its upper surface at 14 into the top of steam nozzle 6. The end of the mixing chamber opposite 14 likewise is generally cylindrical as shown in FIG. 2 at 17 with a bore 18 having vertical slot 19 therein. Slots 15 and 19 are in line with channel 11, so that a passageway is formed from the steam nozzle 6 through passageway 7, orifice 8, slot 15, channel 11 slot 19 and bore 18. Mounted in the upper end of 17 and concentric therewith is venturi tube 20. Pressurized gas, such as for example air, oxygen, oxygen-enriched air, or other gas is passed through 20 into bore 18. It will be seen from FIG. 3 that baffle 12 terminates above the top surface of boiling unit 3 so as to leave free a passage through which ambient air can be aspirated by the steam flowing around the baffle.

Mist laden air from channel 11 with additional ambient air entering through an opening 21 in the top of housing 10 near cylindrical end 17, are aspirated into bore 18 through slot 19 therein. Fitting over cylindrical end 17 at the lower end is a connection consisting of tube 22 having a lateral arm 23, forming a T. Above arm 23, in tube 22 is a port 24 adapted to receive a carrier, such as a rod 25 which is coated with a volatile medicament which can vaporize in the warm stream of mist flowing past it. Various antibacterial and decongestant agents may be employed for use of the invention in treating respiratory ailments, as for example a mixture of camphor, menthol and petrolatum. Rod 25 is coated with a pre-measured dosage by merely dipping the rod into the medicament, which is in the form of a jelly.

Figure 6:
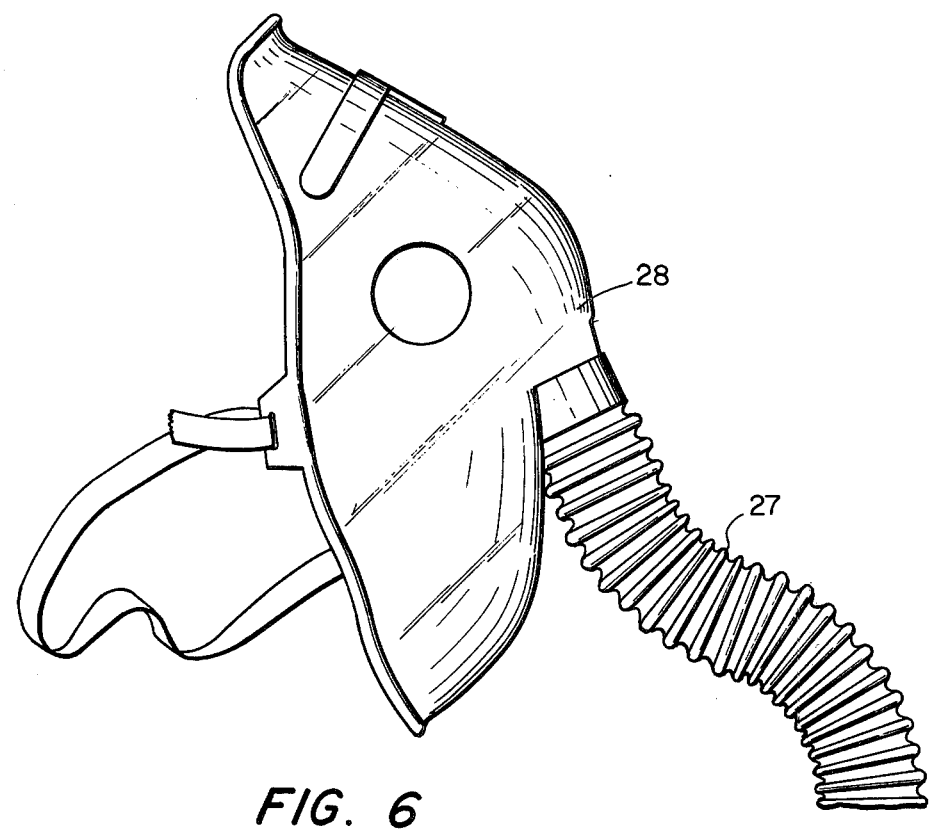
FIG. 6 shows a face mask connected to the inhalator.
Figure 7:
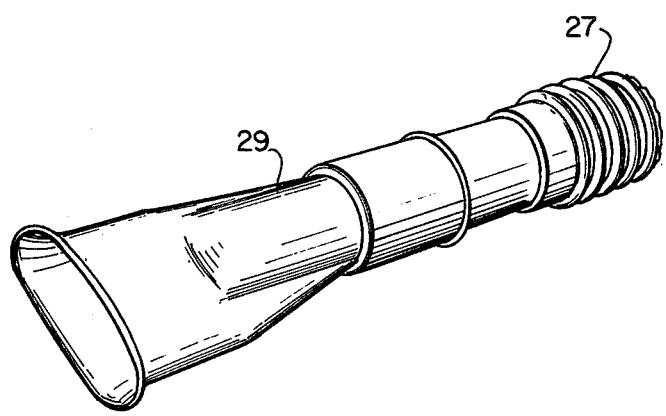
FIG. 7 shows a mouth piece for connection to the inhalator.

The lower end 26 of tube 22 extends through top surface 2 below the level of water in the reservoir and serves to return condensate thereto. Attached to the side arm 23 is flexible tube 27 attached to a conventional face mask 28, (FIG. 6) or to a mouth piece 29 (FIG. 7).

The amount of steam evolving from the generator and the flow rate of pressurized gas should be so chosen as to let the mixture of superfine mist and gas to arrive at the face mask or mouth piece at about body temperature, i.e. approximately 37° C. By way of example and without any intention to limit the invention to the following parameters, I have found that air delivered to the venturi tube 20 at about 2 psi and 200 cu. in. per minute is satisfactory.

The amount of steam entering the breathing element as well as the temperature of the mixture of gas and mist entering side arm 23 may be raised or lowered by reducing or enlarging the size of the channel and accordingly, thereby lower or raise the temperature. Variation of the steam flow may likewise be accomplished by changing the depth of baffle 12. A shallower baffle would allow more steam to pass and thus increase the temperature, while the converse would hold with a longer baffle. Altering the size of opening 21 to vary the amount of ambient air entering the channel through said opening would likewise serve to control the temperature; an increase in the diameter would admit more ambient air and hence lower the temperature, and vice versa.

Returning any condensate formed to the water reservoir enables vaporizer to be used for periods as long as eight hours or more without refilling. In addition, removal of the condensate before it enters the breathing element avoids exposing the patient to the discomfort of having condensate dripping on his body and clothing, so that a long exposure time can be comfortably tolerated.

What is claimed:

1. In combination:
   a. a vaporizer comprising an enclosed reservoir containing water and having a top cover, steam generating means, and a steam outlet nozzle leading from said generating means,
   b. a steam-air mixing chamber comprising a housing having an internal channel with a first and a second end,
   c. a generally transverse baffle partially obstructing said channel between said first and second ends,
   d. said steam nozzle removably fitted into said first end of said housing and having an outlet orifice directed towards said channel to direct a steam jet onto said baffle,
   e. said housing having entrance means for ambient air in the vicinity of the baffle, whereby ambient air can enter into said channel, and whereby the steam is deflected by said baffle, and entrains and mixes with the ambient air to form a superfine mist,
   f. venturi inlet means in said housing near said second end thereof and connected to a source of pressurized gas,
   g. said second end of said housing defining a tubular means said inlet means axially aligned with said tubular means at said second end of said housing and passing pressurized gas into said tubular means,
   h. said tubular means communicating with said channel,
   i. a tubular fitting having two ends and a lateral arm in communication therewith, said tubular fitting removably connected at one end to said tubular means,
   j. whereby a warm mixture of superfine mist and gas enters said lateral arm from said tubular means,
   k. breathing means connected to said lateral arm,
   l. and the other end of said tubular fitting passing through said reservoir top cover.

2. The combination of claim 1 comprising further a condensate tube connected to the other end of said tubular fitting and extending below the surface of the water in said reservoir.

3. The combination of claim 2 wherein said tubular fitting has a port and a carrier for volatile medicament, said carrier mounted in said port whereby the mist conveyed to said breathing means contains medicated vapors.

4. The combination of claim 3 wherein said steam generating means comprises a pair of electrodes mounted in a separate self-contained removable unit having a top surface, said unit being adapted to fit within an opening in said top surface of said reservoir, and wherein said steam outlet nozzle is mounted on said top surface of said unit.

5. The combination of claim 3 wherein said breathing means comprises a face mask.

6. The combination of claim 3 wherein said breathing means comprises a mouth piece.

7. The combination of claim 3 wherein the compressed gas comprises an oxygen rich gas.

8. The combination of claim 3 wherein said steam jet is normal to said baffle.

9. The combination of claim 1 wherein said tubular fitting has a port and a carrier for volatile medicament, said carrier mounted in said port whereby the mist conveyed to said breathing means contains medicated vapors.

10. The combination of claim 1 wherein a variation in at least one of the following parameters serves to alter the temperature of the mixture of superfine mist and air: the size of said channel, the size of said entrance means for ambient air in said channel, or depth of said baffle.

* * * * *